(12) United States Patent
Zaidi et al.

(10) Patent No.: US 11,559,692 B2
(45) Date of Patent: Jan. 24, 2023

(54) ELECTRODE DEVICES FOR NEUROSTIMULATION

(71) Applicant: GALVANI BIOELECTRONICS LIMITED, Brentford (GB)

(72) Inventors: Faisal Zaidi, Brentford (GB); Sebastien Ouchouche, Brentford (GB)

(73) Assignee: Galvani Bioelectronics Limited, Brentford (GB)

( * ) Notice: Subject to any disclaimer, the term of this patent is extended or adjusted under 35 U.S.C. 154(b) by 153 days.

(21) Appl. No.: 16/634,620

(22) PCT Filed: Jul. 23, 2018

(86) PCT No.: PCT/GB2018/052077
§ 371 (c)(1),
(2) Date: Jan. 28, 2020

(87) PCT Pub. No.: WO2019/020986
PCT Pub. Date: Jan. 31, 2019

(65) Prior Publication Data
US 2020/0230421 A1    Jul. 23, 2020

Related U.S. Application Data

(60) Provisional application No. 62/538,434, filed on Jul. 28, 2017.

(51) Int. Cl.
*A61N 1/05*       (2006.01)
*A61N 1/372*     (2006.01)
(Continued)

(52) U.S. Cl.
CPC .............. *A61N 1/372* (2013.01); *A61K 31/56* (2013.01); *A61N 1/05* (2013.01); *A61N 1/0556* (2013.01); *A61N 1/375* (2013.01)

(58) Field of Classification Search
CPC .......... A61N 1/375; A61N 1/372; A61N 1/05; A61N 1/0556
See application file for complete search history.

(56) References Cited

U.S. PATENT DOCUMENTS 5,003,992 A * 4/1991 Holleman ............ A61N 1/0568
                                                                600/377
6,181,971 B1   1/2001  Doan
(Continued)

FOREIGN PATENT DOCUMENTS

EP    0865800 A2   9/1998
EP    1935448 A1   6/2008
(Continued)

OTHER PUBLICATIONS

International Preliminary Report on Patentability for Application No. PCT/GB2018/052074, dated Jan. 28, 2020, 6 pages.
(Continued)

*Primary Examiner* — Alyssa M Alter
(74) *Attorney, Agent, or Firm* — Merchant & Gould P.C.

(57) ABSTRACT

An extravascular neural interface is disclosed containing electrodes for neurostimulation of the vessel. The devices are housed in flexible substrates, each substrate having a spinal portion for routing leads/conductors into the device for connection to the electrodes. Extending from opposite sides of the spinal portion is a self-sizing inner flap that supports and positions the electrodes to be inward facing, i.e., extravascular designs, and one more rigid outer flap. The electrodes may be flexible multifilar coil electrodes.

12 Claims, 6 Drawing Sheets

(51) Int. Cl.
    *A61K 31/56*     (2006.01)
    *A61N 1/375*     (2006.01)

(56) References Cited

U.S. PATENT DOCUMENTS

| | | | |
|---|---|---|---|
| 6,292,703 B1 * | 9/2001 | Meier | A61B 5/287 607/118 |
| 7,676,275 B1 | 3/2010 | Farazi et al. | |
| 8,155,757 B1 | 4/2012 | Neisz et al. | |
| 8,515,520 B2 * | 8/2013 | Brunnett | A61B 5/296 600/373 |
| 2006/0041277 A1 | 2/2006 | Deem et al. | |
| 2008/0103545 A1 | 5/2008 | Bolea et al. | |
| 2010/0268311 A1 | 10/2010 | Cardinal et al. | |
| 2012/0022617 A1 | 1/2012 | Tockman et al. | |
| 2013/0150933 A1 | 6/2013 | Pianca et al. | |
| 2013/0289686 A1 | 10/2013 | Masson et al. | |
| 2014/0188202 A1 | 7/2014 | Zarembo et al. | |

FOREIGN PATENT DOCUMENTS

| | | |
|---|---|---|
| WO | WO-2008048471 A2 | 4/2008 |
| WO | WO-2009135075 A1 | 11/2009 |
| WO | WO-2014018092 A1 | 1/2014 |

OTHER PUBLICATIONS

International Preliminary Report on Patentability for Application No. PCT/GB2018/052075, dated Jan. 28, 2020, 8 pages.
International Preliminary Report on Patentability for Application No. PCT/GB2018/052077, dated Jan. 28, 2020, 7 pages.
International Search Report and Written Opinion for Application No. PCT/GB2018/052075, dated Oct. 8, 2018, 11 pages.
International Search Report and Written Opinion for Application No. PCT/GB2018/052077, dated Oct. 15, 2018, 9 pages.
International Search Report for Application No. PCT/GB2018/052074, dated Nov. 6, 2018, 2 pages.
International Search Report for Application No. PCT/GB2018/052077, dated Oct. 15, 2018, 2 pages.

* cited by examiner

FIG. 3A
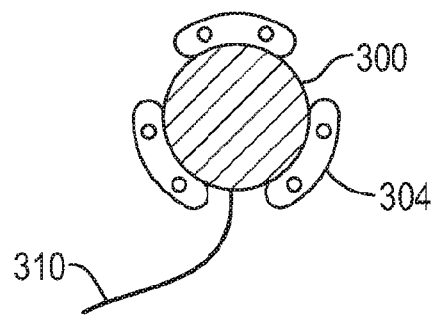
FIG. 3B
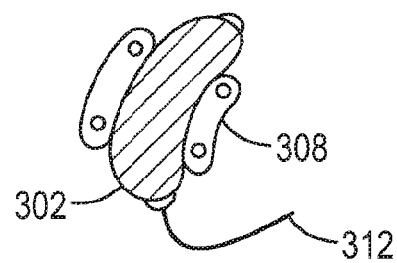
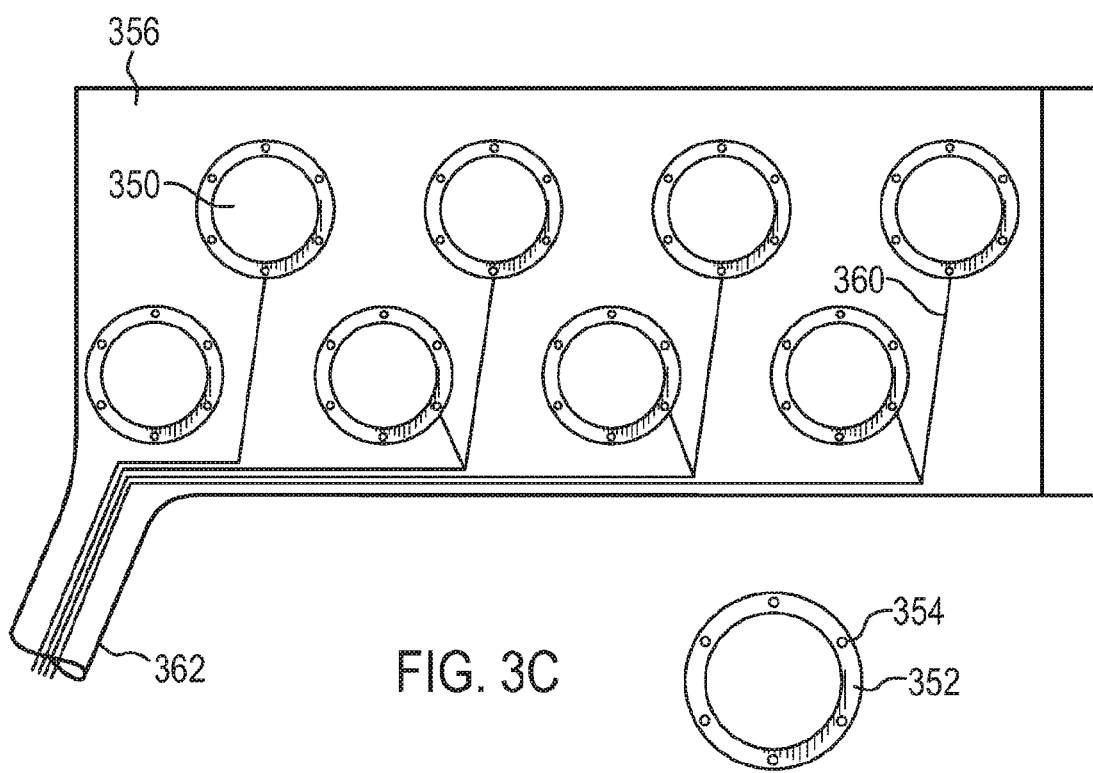
FIG. 3C

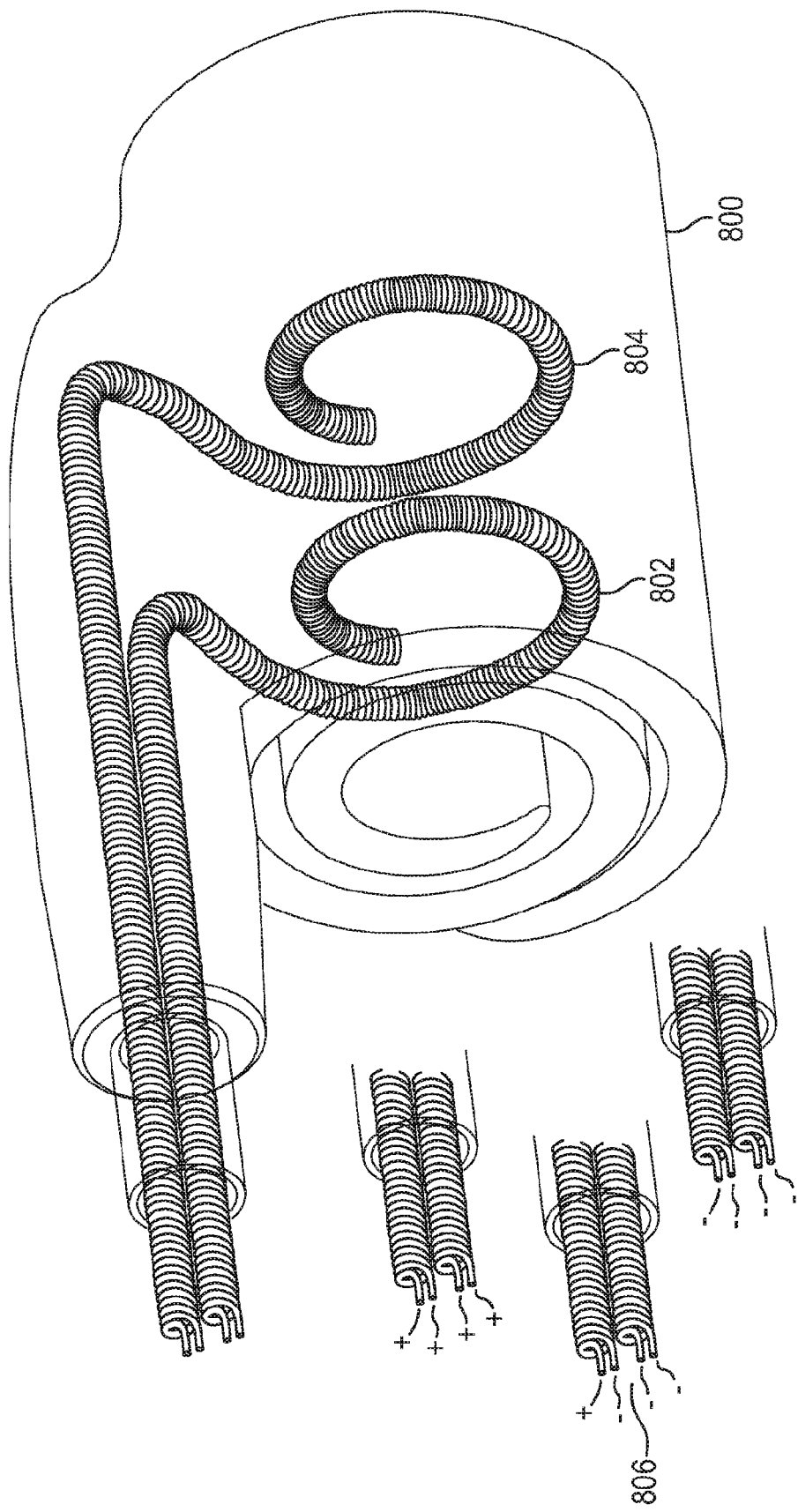

ELECTRODE DEVICES FOR NEUROSTIMULATION

PRIORITY CLAIM

The present application is a National Phase entry of PCT Application No. PCT/GB2018/052077, filed Jul. 23, 2018, which claims priority from U.S. Provisional Application No. 62/538,434, filed Jul. 28, 2017, which is hereby fully incorporated herein by reference.

BRIEF DESCRIPTION

The present disclosure is related to embodiments of extravascular devices containing electrodes for neurostimulation of a vessel. The devices are housed in flexible substrates, each substrate having a spinal portion for routing leads/conductors into the device for connection to the electrodes. Extending from opposite sides of the spinal portion is a self-sizing inner flaps that support and position the electrodes to be inward facing, i.e., extravascular designs, and one more rigid outer flaps. The electrodes may be flexible multifilar coil electrodes. Extravascular devices are arranged to be positioned on the outside of the target vessel, or at least partially.

BACKGROUND

Electrical devices of various shapes and sizes including one or more electrodes have been used for neurostimulation of target anatomy for years. U.S. Pat. No. 7,231,260 discloses an intravascular device that includes a single flap with a few electrodes that can be collapsed (rolled up) to fit within a catheter for implantation, and which expands outside of the catheter to cover a portion (less than 360 degrees) of the inside walls of a target vessel. To keep the flap in place against the target vessel wall, the flap itself may be an arcuate resilient spring formed of polyimide, polytetrafluoroethylene, fluorinated ethylene propylene, polyethylene or silicone, or include a plurality of resilient spring loops mounted to the flap to apply pressure against an opposing wall, thereby pushing the flap against the opposing target vessel wall.

The above illustrates existing designs with flaps that cover a portion of the interior circumference of a target vessel. Such designs fail to cover the entire circumference of the target vessel and lack radial flexibility and self-sizing capabilities relative to the entire target vessel. If the target vessel is excessively compressed by the device, nerve damage may result from the decreased blood flow and constricted nerve fibers. Temporary swelling of the target vessel caused by the trauma of the positioning of the device can exacerbate such nerve damage. In contrast, loose fitting devices can result in poor electrical contact and low treatment efficiency, which can further degrade over times as a result of ingrowth of connective tissue between the target vessel and the device.

In Zaidi F. N., Meadows P., Jacobowitz O., Davidson T. M., 2012, *Tongue Anatomoy and Physiology, the Scientific Basis for a Novel Targeted Neurostimulation System Designed for the Treatment of Obstructive Sleep Apnea*, Neuromodulation 2013; 16: 376-386, a six contact self-sizing, spiral cuff electrode is briefly described in which six independent current sources are used to separately control six separate electrodes in the cuff electrode. The electrodes are arranged in the material of the cuff and aligned so that a spiral circumference of the nerve is contacted by an electrode. Each of the electrodes includes one or more wings around a periphery that may be used to secure the electrodes within the cuff material. U.S. Pat. Nos. 8,886,322 and 9,579,505 and U.S. Pat. App. Pub. No. US 2014/0236255 A1 further illustrate and describe the same overlapping cuff design for treatment of the Hypoglossal nerve, but which does not address all of the limitations of conventional devices.

Conventional helical or serpentine electrode devices further address some of the limitations of conventional rigid cuff-like and cage-like devices, such as permitting some radial expansion that helps with post-operative edema or swelling of the target vessel, more fluid exchange with surrounding tissue, better electrical contact, and reduced growth of connective tissue. Helical or serpentine devices, however, require a complex positioning that requires significant dissection and nerve manipulation in order to wind the helix around the nerve at least two times. Positioning of such devices also requires mobilization of a large portion of the nerve because the cathode and anode electrodes are typically positioned by their own device.

Cuff-like devices require electrodes that provide maximum electrode coverage while being radially compliant. The term "compliant" as used herein refers to the amount of flexibility and/or give that an object might have and particularly in reference to its ability to interact with other objects. For example, when a first object puts physical pressure on a second object intended to work with the first object, the second object is compliant if it is capable of adjusting to that physical pressure, while continuing to perform its intended function. Conventional electrodes used for this purpose include very thin metal sheet electrodes, segmented metal contacts, and thin-film based electrodes. Thin metal sheets can be difficult to connect to leads, provide limited radial compliance and are prone to breakage if excessive stress is applied to the cuff (i.e., from opening and closing). Segmented contact electrodes increase the complexity of manufacturing the cuff and provide limited electrode coverage. Thin film based electrodes can also be difficult to interconnect to lease and are prone to delamination.

SUMMARY

In one aspect of the disclosure there is a neural interface for interfacing with a target vessel, the neural interface comprising: a spinal portion configured to house electrical leads for one or more electrodes and configured to provide a supporting structure; a flexible inner flap connected to at least a first side of the spinal portion and configured to house and position the one or more electrodes around the target vessel; and an outer flap connected a second side of the spinal portion and configured to overlap the flexible inner flap, wherein the first side is opposite the second side, wherein the outer flap is more rigid than the flexible inner flap, wherein the outer flap and the flexible inner flap are configured to create a mechanically lock between the outer flap and the flexible inner flap.

Thus, by using an inner and an outer flap rather than a single flap, the neural interface is able to cover the entire circumference of the target vessel, which can improve the electrical coverage provided by the neural interface and the stability of the interface between the neural interface and the target vessel. Also, the neural interface can be positioned on the target vessel in a simple manner.

The inner flap of the neural interface may be non-rigid and capable of elastic deformation (i.e. reversible deformation). In this way, the inner flap can be displaced from an initial resting state into a different state in order to position the interface with respect to the target vessel. The inner flap is, therefore, biased towards the initial resting state. Then, when the interface is in an appropriate position the interface can be released allowing the inner flap to be urged back to its resting state, thus softly gripping the target vessel. The inner flap is capable of radial flexibility. Thus, if the target vessel is excessively compressed by the device, nerve damage may result from the decreased blood flow and constricted nerve fibers. Temporary swelling of the target vessel caused by the trauma of the positioning of the neural interface can exacerbate such nerve damage. In contrast, loose fitting interfaces can result in poor electrical contact and low treatment efficiency, which can further degrade over times as a result of ingrowth of connective tissue between the target vessel and the interface.

The outer flap is more rigid than the flexible inner flap (i.e. the outer flap is less flexible than the flexible inner flap). In this way, the outer flap provides stability while the inner flap is able to softly grip the target vessel.

The spinal portion comprises an elongate member comprising a conduit for electrical conductors for the first electrode and the second electrode. In some examples, the spinal portion includes the electrical conductors. The spinal portion provides a simple and convenient arrangement for providing electrical connectivity to the first electrode and the second electrode.

In some aspects of the disclosure, the one or more electrodes are housed in the flexible inner flap. Also, the electrical leads may be housed in the spinal portion and may be connected to respective one or more electrodes.

In another aspect of the disclosure there is a method of manufacturing a neural interface, the method comprising: covering a length of a lead with a tube except for a first end of the lead; connecting the first end of the lead to an elongated electrode; placing at least a portion of the length of the lead, the first end of the lead and the elongated electrode in a first mold; molding via the first mold a first material over at least the portion, the first end of the lead and the elongated electrode to create a flexible inner flap and a spinal portion of the neural interface, wherein at least a portion of a length of the elongate electrode is exposed from the first material on an inside surface of the flexible inner flap; and molding via a second mold a second material to create an outer flap of the neural interface, the outer flap covering at least a portion of the flexible inner flap, wherein the outer flap and the flexible inner flap are configured to create a mechanically lock between the outer flap and the flexible inner flap.

Thus, it is possible to manufacture the neural interface in a simple and efficient manner.

In another aspect of the disclosure there is a coil electrode for a neural interface, the coil electrode comprising: a central portion extending from a proximate end of the coil electrode to a distal end; two or more filar spirally wound around the central portion from the proximate end to the distal end, wherein the two or more filar are connected to a lead for controlling the coil electrode at the proximate end; and a plug at the distal end for terminating the two or more filar.

Thus, it is possible to improve the amount of surface area of the electrode that is in contact with the target vessel.

In the present disclosure, a vessel refers to a vessel and a nerve (or nerves) that travels along with the vessel. The vessel may be an artery (or arteries) and/or a vein (or veins) and/or a lymph vessel (or lymph vessels). A nerve that travels along a vessel may be a nerve that is adjacent to the vessel or a nerve that is in the vicinity of the vessel.

In the present disclosure, a target vessel may be a target vessel that includes a nerve (or nerves) that travels along with the vessel. The target vessel may be an artery (or arteries), and/or a vein (or veins), and/or a lymph vessel (or lymph vessels).

BRIEF DESCRIPTION OF THE SEVERAL VIEWS OF THE DRAWING

FIG. 3A, FIG. 3B and FIG. 3C illustrate a variety of different electrodes with extending wings or spikes or protruding bites for enabling the electrodes to be embedded between sheets of the flap structure;

FIG. 8 is a perspective view of a neural interface including a plurality of multifilar coil electrodes in accordance with an embodiment,

DETAILED DESCRIPTION

The present disclosure is related to embodiments of extravascular devices containing electrodes for neurostimulation of a vessel. The devices are housed in flexible substrates, each substrate having a spinal portion for routing leads/conductors into the device for connection to the electrodes. Extending from opposite sides of the spinal portion is a self-sizing inner flaps that support and position the electrodes to be inward facing, i.e., extravascular designs, and one more rigid outer flap. The electrodes may by flexible multifilar coil electrodes. By "self-sizing" it is meant that the neural interface 100 conforms to the shape of the target vessel of its own accord.

Figure 1A:
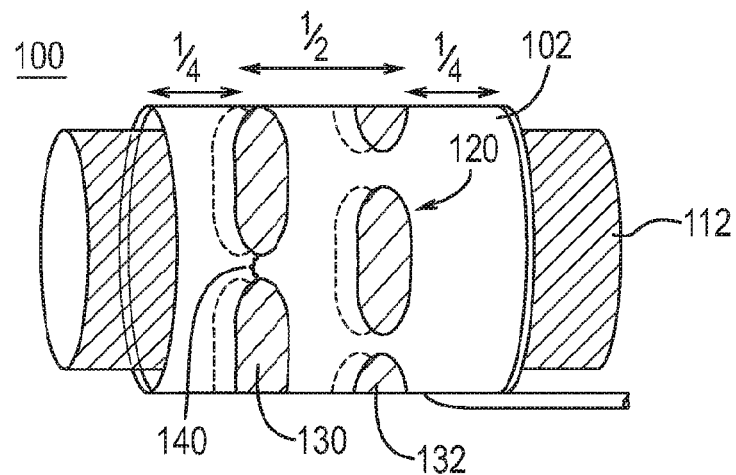
FIG. 1A is a perspective view of an embodiment of an extravascular neural interface device including a flexible overlapping flap structure holding and positioning a plurality of elongated elliptical (curved) electrodes.
Figure 1B:
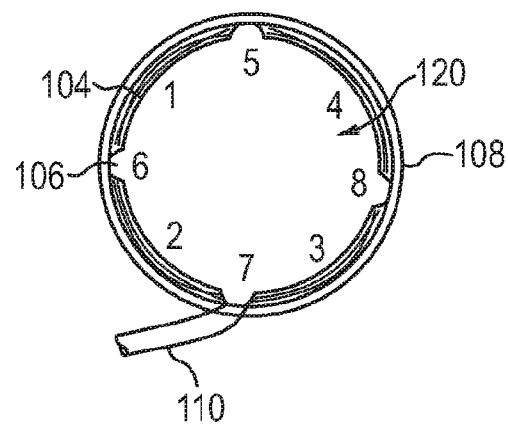
FIG. 1B is an end view of the embodiment of FIG. 1A.

An embodiment of a bi-polar, extravascular neural interface 100 in accordance with the present disclosure is illustrated in FIG. 1A and FIG. 1B. The neural interface 100 may comprise a self-sizing cuff 102 that is formed of a supporting substrate manufactured of silicone or a similar flexible substance (e.g., with a hardness of Shore A20 to A70, where "hardness" generally refers to a measure of how resistant solid matter is to permanent shape change when a compressive force is applied, which hardness of the material may be measured with a durometer), such as styrene isoprene butadiene (SIBS), polyamide, parylene, liquid-crystal polymer (LCF), polytetrafluoroethylene (PTFE), polyethylene (PE), polypropylene (PP), fluorinated ethylene propylene (FEP), ethylene-tetrafluoroethylene (ETFE), polyurethane, or another biocompatible polymer. As shown in FIG. 1B, the cuff 102 may include an inner flap 104, with a tapering end 106 and an outer flap 108.

The inner flap 104 may include a spinal portion or spine 110 that houses leads or conductors for each of the electrodes. The flaps may be positioned orthogonal to the length of the target vessel (not shown) around which the flaps may be ultimately wrapped or may be positioned at an angle, such as 45 degrees relative to the length. The inner flap 104 may be wrapped around the target vessel and the outer flap 108 may then be wrapped around the inner flap 104.

Figure 2:
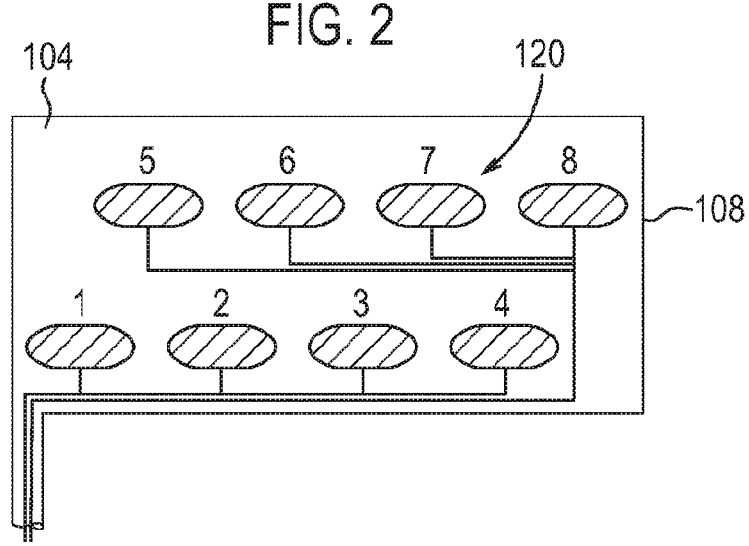
FIG. 2 is a side view of the embodiment of FIG. 1A.

Housed and positioned within the inner flap 104 may be a series of 8 or more substantially elliptical curved electrodes 120 that may be staggered so as to form a circular pattern around the target vessel when the neural interface 100 has been positioned and closed around the target vessel. For example, FIG. 2 illustrates the series of electrodes 120 labeled from 1 to 8, with one column of electrodes (1-4) substantially opposite, yet offset from, a second column of electrodes (5-8), while FIG. 1B illustrates the resulting arrangement of the 8 electrodes from an end view. FIG. 1A illustrates the series of electrodes 120 positioned to form a staggered circular ring pattern around the target vessel 112. FIG. 2 illustrates the electrodes 120 when the inner flap 104 and the outer flap 108 are laid on a flat surface, such that once electrodes (1-4) are rolled over electrodes (5-8), the 8 electrodes will be arranged as shown in FIG. 1A.

The series of electrodes 120 may be positioned in a selective or non-selective layout and may include a positive left hand spiral column and a negative right hand spiral column, or may be formed in any other combination or arrangement. The electrodes 120 may be platinum or platinum alloy electrodes (or electrode arrays). The electrodes 120 may be of a conventional type and wired to a controller through conventional conductors, such as 35N LT® DFT (Drawn Filled Tubing) with a 28% Ag core, in a stranded cable configuration or in a multi-filar coil configuration. The conductors are housed in spinal portion or spine 110.

The "segmented" electrode designs may provide better mechanical compliance, create the possibility of surface features, i.e., protruding electrodes, and make it possible to control each electrode individually (i.e., current steering). For example, connecting individual electrodes or different arrays of electrodes to different conductors may enable selective stimulation of the target vessel by individually controlling each connected device. Individual electrodes, if wired separately, may be selected and activated for power/current grading of a stimulation field of the target vessel. In addition, the polarity of the electrodes may be controlled independently. For example, all of the electrodes in a first row of electrodes 130 may have a negative polarity while all of the electrodes in a second row of electrodes 132 may have a positive polarity, or the negative and positive polarity may be mixed in both of the rows of electrodes 130 and 132.

The electrodes 120 may also be positioned in an overlapping fashion, such that no electrical transverse gaps are created between the electrodes in rows 130 and 132. For example, in FIG. 1A, the electrodes in the row 130 may be offset from the electrodes in the row 132 so as to cover at least a helical turn of the electrodes 130 when the neural interface 100 is positioned, which also prevents any transverse gaps between the rows. In other words, when the neural interface is positioned on the target vessel there is no longitudinal axis/plane along the length of the interior or exterior surface of the target vessel that does not pass through an electrode over at least a 360 degree turn around an interior surface or an exterior surface of a target vessel.

Aligning individual electrodes or arrays of electrodes so as to remove electrical transverse gaps, say between two rows of electrodes or some other arrangement, may insure complete electrical coverage of the target vessel over a length of the target vessel. For example, as illustrated in FIG. 1A, a total of 8 coiled platinum electrode rows or strips may be utilized in each neural interface. Neural interface 100 may also be configured for intravascular applications by locating the electrodes along exterior surfaces of the neural interface 100.

Other electrode shapes may also be used. For example, each of the substantially circular electrodes 300 and the substantially elliptical curved electrodes 302 are further illustrated in FIG. 3A and FIG. 3B, respectively. As illustrated in FIG. 3A, each electrode 300 may include a plurality of wings 304 that may include a number of holes/bites/protrusions in each wing. The inner flap 104 may be manufactured from sheets of substrate material. The electrode 300 may be connected to lead wired 310 and positioned on a first sheet of the inner flap 104. Glue or silicone may be used to fill the holes of the wings 304 before a second sheet is applied over the top. In an embodiment, the electrodes 300 may be positioned on a sheet and have a second sheet reflowed over the top to fill the holes of the wings. Sheet material covering the electrodes may be laser ablated, if necessary, to expose the surface of the electrode. In an embodiment, the first or second sheet may have holes preformed in the sheet to indicate the position of each electrode and to expose the surface of the electrode, as necessary, relative to the second sheet.

As illustrated in FIG. 3B, each electrode 302 may include a plurality of wings 308 that may include a number of holes/bites/protrusion in each wing. The inner flap 104 may be manufactured from sheets of substrate material. The electrode 302 may be connected to lead wired 312 and positioned on a first sheet of the inner flap 104. Glue or silicone may be used to fill the holes of the wings 308 before a second sheet is applied over the top. In an embodiment, the electrodes 302 may be positioned on a sheet and have a second sheet reflowed over the top to fill the holes of the wings. Sheet material covering the electrodes may be laser ablated, if necessary, to expose the surface of the electrode. In an embodiment, the first or second sheet may have holes preformed in the sheet to indicate the position of each electrode and to expose the surface of the electrode, as necessary, relative to the second sheet.

As illustrated in FIG. 3C, each substantially circular electrode 350 has a substantially circular ring 352, essentially a continuous wing, attached to and positioned around the electrode 350. The ring 352 includes a number of holes 354 around the ring 352, which may be filled with glue or silicone, as discussed above, in order to hold the electrode 350 in position within the inner flap 356. As illustrated in FIG. 24 and FIG. 3C, the lead wires from each electrode may be routed through the sheets of the inner flap to a spinal portion or spine. For example, as shown in FIG. 3C, the leads 360 of each electrode 350 is routed in-between the sheets of the inner flap 356 to spinal portion or spine 362 and then away from the device to a controller (not shown).

Figure 4A:
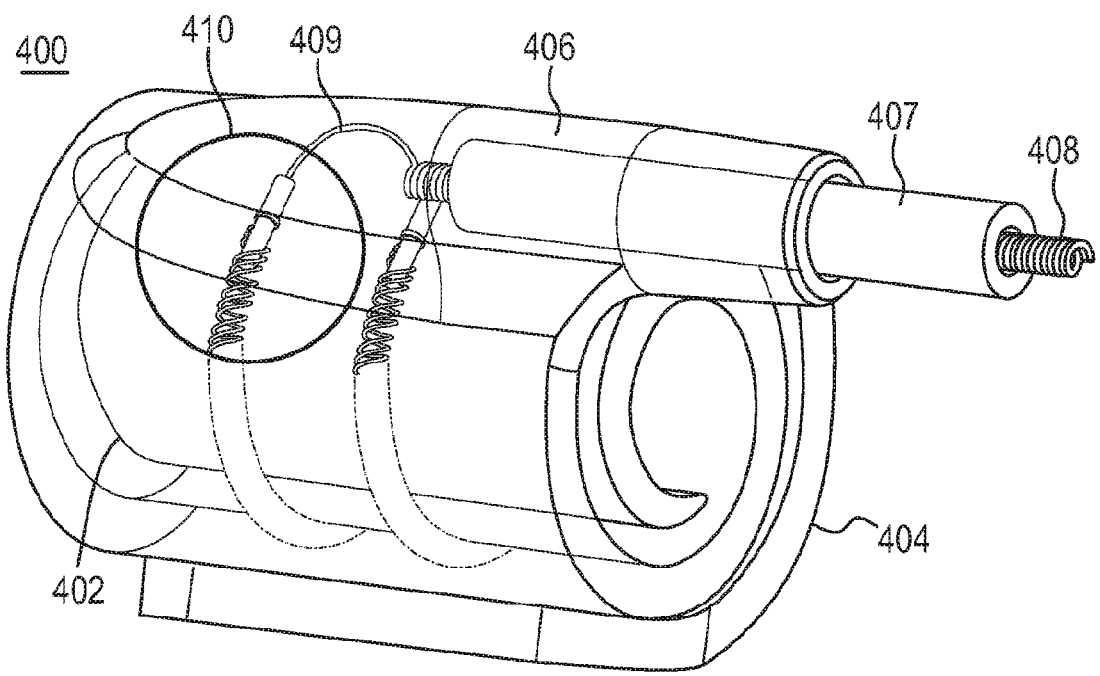
FIG. 4A is a perspective view of an embodiment of an extravascular neural interface device including a flexible overlapping flap structure holding and positioning coil electrodes.
Figure 4B:
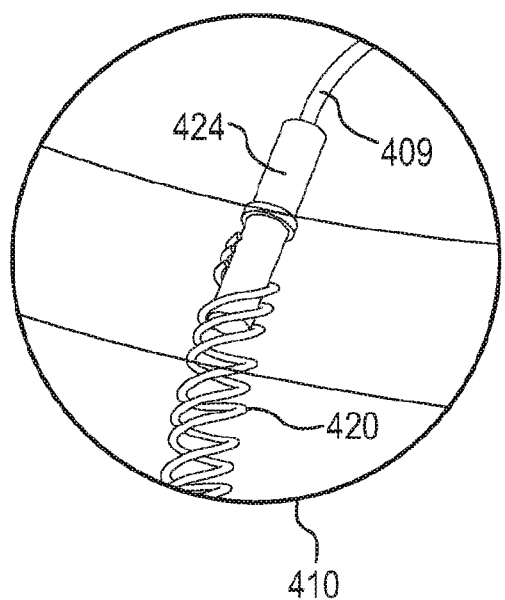
FIG. 4B is a detailed view of the interface connecting the coil electrode to the conductor.

The overlapping flaps of the cuff of the neural interface may also be manufactured with coil electrodes, further illustrated with reference. FIG. 4A illustrates a cuff 400 of an extravascular neural interface device similar to those already described above. For example, the cuff 400 may include an inner flap 402 and an outer flap 404 connected to a spinal portion or spine 406. The spine 406 may include a silicone tubing 407 through which the leads/conductors of the electrodes may be housed and routed, with the individual leads 409 for each electrode exiting a distal end of the tubing 407. The circled area 410 of FIG. 4A is further illustrated in FIG. 4B. As shown therein, the lead 409 may by connected to the coil electrode 420 by a crimp/weld sleeve 424.

Figure 5:
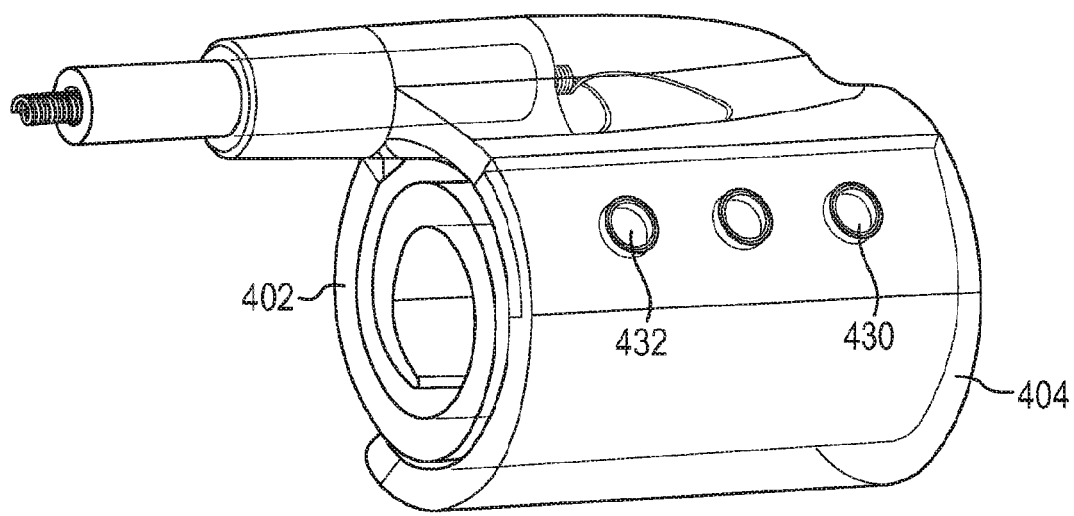
FIG. 5 is a perspective view of the embodiment of FIG. 4A further illustrating the outer flap of the neural interface device.

The electrode 420, sleeve 424, conductor 408, lead 409 and tubing 407 may be preassembled and positioned within a mold prior to formation of the remainder of the cuff 400. Once those components are positioned in the mold, the inner flap 402 and the spinal portion or spine 406 may be molded over those components. In an embodiment, inner flap 402 and spinal portion or spine 406 may be molded at a shore hardness of approximately 20 A so as to be compliant and self-sizing. In an embodiment, after molding the inner flap 402, the outer flap 404, which is further illustrated in FIG. 5, may be molded at a shore hardness of approximately 75 A. As shown in FIG. 5, the outer flap 404 may include a set of holes 430 through which protrusions 432 formed in the molding of inner flap 402 may be inserted. In such an embodiment, a portion of the inner flap 402, sufficient to support the protrusions 432, may be formed on a first side of the spinal portion/spine 406 while the remainder of the inner flap is formed on the second (opposite) side of the spinal portion/spine 406. The outer flap 404 may then be formed on the first side over the portion of the inner flap 402 on that same side, with the protrusion extending through the holes 430, which is configured to enable the inner flap 402 to be mechanically locked to the more rigid outer flab 404. The shore hardness referred to above may be measured with a durometer. In this example, the mechanical lock is provided by protrusions and holes; however, it will be appreciated that the mechanical lock could be provided by another suitable arrangement that would be apparent to the skilled person.

Figure 6:
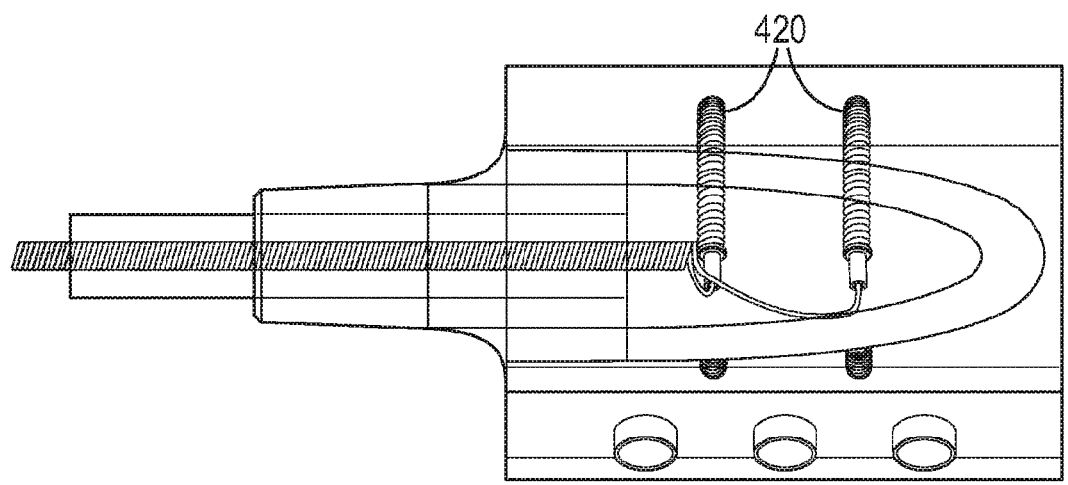
FIG. 6 is a top view of the embodiment of FIG. 5.
Figure 7A:
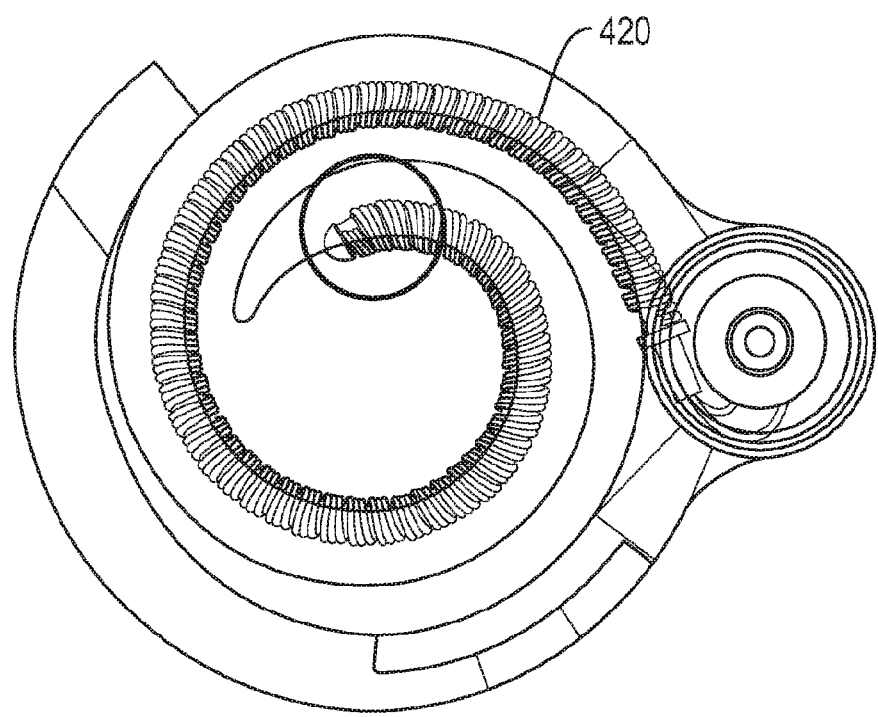
FIG. 7A illustrates a side view of the embodiment of FIG. 6.

As further illustrated in FIG. 6, there may be multiple electrodes 420, although only two are shown therein, connected to the lead wires 409 of the conductor 408. The electrodes 420 may be positioned in a central area of the cuff 400 and spaced appropriately from one another. As further Illustrated in FIG. 7A, the electrode 420 may be exposed at the interior surface of the inner flap 402 (i.e., only partially embedded, hence slightly protruding) so as to make good contact with the surface of the target vessel and largely follow the along the width of the inner flap 402. In addition, the topology of the surface of the electrode 420 leads to a greater active surface of the electrode 420 compared to conventional flat electrodes. For instance, for the same footprint, a coil electrode can provide two times more exposed electrode surface.

Figure 7B:
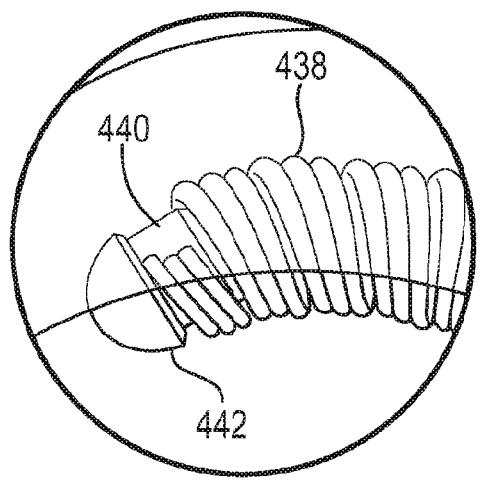
FIG. 7B is a detailed view of the distal end of the coil electrode of FIG. 7A.

The electrodes 420, as illustrated in FIG. 7B, may include one or more filars 438 wrapped in a coil around a central portion 440 and terminated at a laser welded plug 442. The number of filars 438 involves a trade-off between the electrode compliance and electrical resistance of the electrode 406. Increasing the number of filars 438 decreases the radial compliance of the electrode 406 while decreasing the electrode's electrical resistance. Each filar 438 within the electrode 420 may be assigned the same polarity or different polarities.

As illustrated in FIG. 8, a neural interface 800 may include a plurality of multifilar coil electrodes 802 and 804, each of which may have the same or different polarities. In addition, each of the individual filar 806 wrapped around the central portion of each coil electrode 802 and 804 may be configured to have the same or different polarities and individually controlled (including the ability to change polarity when desired), thereby enabling the filar 806 and the coil electrodes 802 and 804 to be selectively stimulated. The polarity of any electrode can be determined by a controller (not shown) providing power to the electrode and is not necessarily dependent on a mechanical structure of an electrode to determine that electrode's polarity. Nevertheless, the electrodes can be configured to have a specific polarity and configured for that polarity to be changed. For example, an electrode could be configured to have a selective negative polarity, i.e., negative polarity is selected, and then be configured, at a later point in time, to have a selective positive polarity.

The compliancy of inner flap 402, which may be molded from silicone or a similar material, is configured such as to allow the inner flap 402 to self-size to target vessels of varying radial width, yet maintain close to 360 degree coverage of the surface of the target vessel. At the same time, the electrodes 420, 802 and 804 may be longitudinally compliant so they can adjust to the self-sizing inner flap. Longitudinal compliance may be achieved by wrapping the filar around the central portion so that the filar can move along the length of the central portion, like a wound spring, as the inner flap moves. The coil electrodes 420, 802 and 804 may at least as flexible as the flexible inner flap, or less flexible than the flexible inner flap. In either case, the coil electrode may be longitudinally compliant.

The material used to mold the inner flap 402 may be doped with a steroid drug, such as dexamethasone. In an embodiment, outer surface of the cuff 00 may also, or alternatively, be coated with a hydrophilic polymer, such as poly-2-hydroeyethyl-methacrylate (pHEMA).

The resulting cuff 400 provides excellent radial compliance because the coil electrode 406 is designed to be as compliant as the material of the inner flap 402, thereby reducing flex fatigue and a tendency to kink or wrinkle as may be the case with conventional electrodes. In addition the coil electrode 406 may stretch and therefore provide a lower radial force, thereby reducing pressure on the nerves of the target vessel. At the same time, the extended length of the coil electrode 406 and its position within the inner flap 402 of the cuff 400 maximize circumferential coverage and active surface coverage. This reduces the need to segment the electrodes in order to increase compliance. Finally, the conductors can be easily connected to the electrodes and is easy to manufacture.

The following is a non-exhaustive list of embodiments that may or may not be claimed:

1. A neural interface, comprising:
   a spinal portion configured to house electrical leads for one or more electrodes and provide a supporting structure;
   a flexible inner flap connected to at least a first side of the spinal portion and configured to house and position the one or more electrodes around a target vessel; and
   an outer flap connected a second side of the spinal portion and configured to overlap the flexible inner flap, wherein the first side is opposite the second side, wherein the outer flap is more rigid than the flexible inner flap, wherein the outer flap and the flexible inner flap are configured to create a mechanically lock between the outer flap and the flexible inner flap.

2. The neural interface of embodiment 1, wherein a first portion of the flexible inner flap is connected to the second side of the spinal portion and includes one or more protrusions on an outer surface of the first portion, wherein a second portion of the flexible inner flap is connect to the first side of the spinal portion and includes the one or more electrodes, and wherein one or more holes are formed in the outer flap and configured to receive the one or more protrusions.

3. The neural interface of embodiment 1, wherein the one or more electrodes is a coil electrode that extends orthogonal to a length of the target vessel when positioned around the target vessel.

4. The neural interface of embodiment 3, wherein the one or more electrodes are configured to be exposed to the target vessel from an inside surface of the flexible inner flap.

5. The neural interface of embodiment 3, wherein the one or more coil electrodes are connected to a lead of the electrical leads by a crimp/weld sleeve.

6. The neural interface of embodiment 3, wherein the one or more coil electrodes include one or more filar wound around a central portion and terminated at a distal end of the central portion at a plug.

7. The neural interface of embodiment 3, wherein the flexible inner flap has a first hardness and the outer flap has a second hardness, and wherein the second hardness is greater than the first hardness.

8. The neural interface of embodiment 7, wherein the spinal portion and the flexible inner flap are molded from a silicone-based material.

9. The neural interface of embodiment 8, wherein the silicone-based material is doped with a steroid drug.

10. The neural interface of embodiment 8, wherein the silicone-based material is coated with a hydrophilic polymer.

11. A method of manufacturing a neural interface, comprising:
    covering a length of a lead with a tube except for a distal end of the lead;
    connecting the distal end of the lead to an elongated electrode;
    placing at least a portion of the length of the lead, the distal end of the lead and the elongated electrode in a first mold;
    molding via the first mold a first material over at least the portion, the distal end of the lead and the elongated electrode to create a flexible inner flap and a spinal portion of the neural interface, wherein at least a portion of a length of the elongate electrode is exposed from the first material on an inside surface of the flexible inner flap; and
    molding via a second mold a second material to create an outer flap of the neural interface, the outer flap covering at least a portion of the flexible inner flap, wherein the outer flap and the flexible inner flap are configured to create a mechanically lock between the outer flap and the flexible inner flap.

12. The method of embodiment 11, wherein the first mold forms one or more protrusions in an outer surface of the flexible inner flap, wherein the second mold forms one or more holes in the outer flap that match the one or more protrusions, and further comprising fitting the one or more protrusions in the one or more holes.

13. The method of embodiment 11, wherein the flexible inner flap has a first hardness and the outer flap has a second hardness, and wherein the second hardness is greater than the first hardness.

14. The method of embodiment 11, wherein the first material is a silicone-based material.

15. The method of embodiment 14, further comprising doping the silicone-based material with a steroid drug.

16. The method of embodiment 14, further comprising coating the silicone-based material with a hydrophilic polymer.

17. The method of embodiment 11, wherein the elongated electrode is a coil electrode that extends orthogonal to a length of the target vessel.

18. The method of embodiment 17, wherein the coil electrode is connected to the lead by a crimp/weld sleeve.

19. The method of embodiment 17, wherein the coil electrode includes one or more filar wound around a central portion and terminated at a distal end of the central portion at a plug.

20. A coil electrode for a neural interface, comprising:
    a central portion extending from a proximate end of the coil electrode to a distal end;
    two or more filar spirally wound around the central portion from the proximate end to the distal end, wherein the two or more filar are connected to a lead for controlling the coil electrode at the proximate end; and
    a plug at the distal end for terminating the two or more filar.

21. The coil electrode of embodiment 20, wherein the coil electrode is configured to be partially embedded in a flexible inner flap of the neural interface and extend orthogonal to a target vessel around which the flexible inner flap is positioned.

22. The coil electrode of embodiment 21, wherein the flexible inner flap includes at least two coil electrodes, one of which is configured to have a positive polarity and one of which is configured to have a negative polarity.

23. The coil electrode of embodiment 21, wherein the coil electrode is at least as flexible as the flexible inner flap.

24. The coil electrode of embodiment 23, wherein the spirally wound two or more filar are longitudinally compliant.

26. The coil electrode of embodiment 21, wherein the coil electrode is less flexible than the flexible inner flap.

27. The coil electrode of embodiment 26, wherein the spirally wound two or more filar are longitudinally compliant.

28. The coil electrode of embodiment 20, wherein the two or more filar include a plurality of filar and each filar among the plurality of filar are configured to have a polarity that may be the same or different from the polarity of other filar.

29. A neural interface, comprising:
    a flexible inner flap configured to positioned completely around a target vessel;
    a rigid outer flap connected to the flexible inner flap; and
    at least one coil electrode including one or more filar spirally wound around a central electrode portion from a proximate end to substantially near a distal end of the central electrode portion, wherein the one or more filar are connected to a lead for controlling the at least one coil electrode, wherein the at least one coil electrode is partially embedded in the flexible inner flap, and wherein the at least one coil electrode includes a plug at the distal end of the central electrode portion for terminating the one or more filar.

30. The neural interface of embodiment 29, wherein the coil electrode extends orthogonal to a length of the target vessel when positioned around the target vessel.

31. The neural interface of embodiment 29, wherein the flexible inner flap includes at least two coil electrodes, one of which is configured to have a positive polarity and one of which is configured to have a negative polarity.

32. The neural interface of embodiment 29, wherein the coil electrode is at least as flexible as the flexible inner flap.

33. The neural interface of embodiment 32, wherein the spirally wound one or more filar are longitudinally compliant.

34. The neural interface of embodiment 29, wherein the coil electrode is less flexible than the flexible inner flap.

35. The neural interface of embodiment 34, wherein the spirally wound one or more filar are longitudinally compliant.

The embodiments of the present disclosure, while illustrated and described in terms of various embodiments, is not limited to the particular description contained in this specification. Additional alternative or equivalent components and elements may be readily used to practice the present disclosure.

What is claimed is:

1. A neural interface for interfacing with a target, the neural interface comprising:
   a spinal portion configured to house electrical leads for one or more electrodes;
   a flexible inner flap connected to at least a first side of the spinal portion and configured to house and position the one or more electrodes such that the one or more electrodes are provided around the target; and
   an outer flap connected to a second side of the spinal portion and configured to overlap at least partially around the flexible inner flap and the target, wherein the first side is opposite the second side, wherein the outer flap is more rigid than the flexible inner flap, wherein the outer flap and the flexible inner flap are configured to create a mechanical lock between the outer flap and the flexible inner flap.

2. The neural interface of claim 1, wherein a first portion of the flexible inner flap is connected to the second side of the spinal portion and includes one or more protrusions on an outer surface of the first portion, and wherein a second portion of the flexible inner flap is connected to the first side of the spinal portion and includes the one or more electrodes.

3. The neural interface of claim 2, wherein one or more holes are formed in the outer flap and configured to receive the one or more protrusions.

4. The neural interface of claim 1, wherein the one or more electrodes is a coil electrode that extends orthogonal to a length of the target when positioned around the target, wherein at least one of:
   the one or more coil electrodes are connected to a lead of the electrical leads by a crimp/weld sleeve; or
   the one or more coil electrodes include one or more filar wound around a central portion and terminated at a distal end of the central portion at a plug.

5. The neural interface of claim 1, wherein the one or more electrodes are configured to be exposed to the target from an inside surface of the flexible inner flap.

6. The neural interface of claim 1, wherein the flexible inner flap has a first hardness and the outer flap has a second hardness, and wherein the second hardness is greater than the first hardness.

7. The neural interface of claim 1, wherein the spinal portion and the flexible inner flap are molded from a silicone-based material, and wherein the silicone-based material is at least one of:
   doped with a steroid drug; or
   coated with a hydrophilic polymer.

8. A method of manufacturing a neural interface, the method comprising:
   covering a length of a lead with a tube except for a first end of the lead;
   connecting the first end of the lead to an elongated electrode;
   placing at least a portion of the length of the lead, the first end of the lead and the elongated electrode in a first mold;
   molding via the first mold a first material over at least the portion, the first end of the lead and the elongated electrode to create a flexible inner flap and a spinal portion of the neural interface, wherein at least a portion of a length of the elongate electrode is exposed from the first material on an inside surface of the flexible inner flap such that the one or more electrodes can be provided at least partially around a target; and
   molding via a second mold a second material to create an outer flap of the neural interface, the outer flap provided at least partially around at least a portion of the flexible inner flap and the target, wherein the outer flap and the flexible inner flap are configured to create a mechanical lock between the outer flap and the flexible inner flap.

9. The method of claim 8, wherein the first mold forms one or more protrusions in an outer surface of the flexible inner flap, wherein the second mold forms one or more holes in the outer flap that match the one or more protrusions, and further comprising fitting the one or more protrusions in the one or more holes.

10. The method of claim 8, wherein the flexible inner flap has a first hardness and the outer flap has a second hardness, and wherein the second hardness is greater than the first hardness.

11. The method of claim 8, wherein the first material is a silicone based material, and the method further comprises at least one of:
   doping the silicone-based material with a steroid drug; or
   coating the silicone-based material with a hydrophilic polymer.

12. The neural interface for interfacing with a target of claim 1, wherein the one or more electrodes are provided at least partially around the target such that the entire circumference of the target is covered by the one or more electrodes.

* * * * *